United States Patent
Kapre et al.

(10) Patent No.: US 8,398,985 B2
(45) Date of Patent: Mar. 19, 2013

(54) ANTIGENIC POLYSACCHARIDES AND PROCESS FOR THEIR PREPARATION

(75) Inventors: Subhash V. Kapre, Pune (IN); Akshay Goel, Pune (IN); Tushar Joglekar, Pune (IN); Sandeep Sharma, Pune (IN)

(73) Assignee: Serum Institute of India Ltd., Pune (IN)

( * ) Notice: Subject to any disclaimer, the term of this patent is extended or adjusted under 35 U.S.C. 154(b) by 509 days.

(21) Appl. No.: 12/597,285

(22) PCT Filed: Sep. 6, 2007

(86) PCT No.: PCT/IN2007/000430
§ 371 (c)(1), (2), (4) Date: Oct. 23, 2009

(87) PCT Pub. No.: WO2008/129559
PCT Pub. Date: Oct. 30, 2008

(65) Prior Publication Data
US 2010/0129881 A1    May 27, 2010

(30) Foreign Application Priority Data
Apr. 23, 2007    (IN) .......................... 786/MUM/2007

(51) Int. Cl.
*A61K 39/00*    (2006.01)

(52) U.S. Cl. ................ 424/184.1; 424/193.1; 424/234.1

(58) Field of Classification Search ........................ None
See application file for complete search history.

*Primary Examiner* — Anand Desai

(74) *Attorney, Agent, or Firm* — Fish & Richardson P.C.

(57) ABSTRACT

A robust and industrial scale process to afford highly pure antigenic polysaccharides is claimed.

19 Claims, No Drawings

ANTIGENIC POLYSACCHARIDES AND PROCESS FOR THEIR PREPARATION

FIELD OF THE INVENTION

The present invention relates to a process for purification of polysaccharides, specifically antigenic polysaccharides.

BACKGROUND OF INVENTION

Polysaccharides, especially antigenic polysaccharides, are used in preparation of vaccines. Monovalent, divalent and poly (multi) valent vaccines containing one, two or more polysaccharides are available in the market for preventions of certain diseases or infections caused by various microorganisms. The multivalent polysaccharide vaccines have been licensed for many years and have proved valuable in preventing diseases such as Pneumococcal, Meningococcal or Haemophilus influenzae diseases. Surveillance data gathered in the years following Prevnar's introduction has clearly demonstrated a reduction of invasive pneumococcal disease in US infants as expected [1, 2]. Despite of several studies carried out on these polysaccharides, a need for improving yields as well as quality (purity) of the polysaccharides always exist in the industry (e.g. Hib, MenC).

Prior inventions, for e.g. EP00024 disclosed methods involving the use of toxic components like Phenol; organic solvents like isopropanol or ethanol; use of detergents like CTAB for polysaccharide precipitation and the use of sodium acetate for pH adjustments.

EP 497525 disclosed a method involving thermal hydrolysis and use of sodium acetate to hydrolyze the sample.

CA 1206905 described a method which uses toxic organic solvents like Phenol, butanol, Toluene and chloroform and also involves use of detergent cetavlon (CTAB).

U.S. Pat. No. 4,242,501 and some more studies [5] mention a method which involves serotype specific anion exchange chromatography.

Classical methods described by Institut Merieux give details of the use of CTAB and protease [6] for purification of N. Meningitidis serogroup A, C polysaccharide purification [7].

Some other methods made use of proteinase for removal of proteins and use of lectin agarose columns resulting in high costs and process which can't be scaled up easily [8, 9].

US 20060228380 as well as some studies [10, 11] disclosed a method which comprises CTAB for polysaccharide (Ps) precipitation, carbon filter for nucleic acid removal and potassium iodide for precipitation of CTAB.

U.S. Pat. No. 5,847,112 disclosed a method which makes use of multiple isopropyl alcohol and cetavlon for the precipitation of PS [12].

The prior art methods can not be applied to all PS for purification since Pneumo Serotypes 7F, 33F and 18C can not be precipitated using CTAB while the remaining serotypes can be precipitated.

Also the prior art methods are multi-step and therefore are tedious and non-scalable.

The present invention aims to present an easily scalable, efficient and fewer steps purification process that eliminates the use of any toxic component, organic solvent and/or detergents. The significant finding of this invention is applicable to purification of all capsular polysaccharides.

SUMMARY OF THE INVENTION

The invention relates to a process for purification of antigenic polysaccharides.

The process of the instant invention comprises following steps in any order:
a) treatment of the solution comprising polysaccharide with ammonium sulphate,
b) treatment of the solution comprising polysaccharide with nuclease,
c) isolation of the polysaccharide by adsorption chromatography.

The process of instant invention can be used to purify any antigenic polysaccharide.

The process exhibits following advantages over prior art:
1. Robust method applicable to any polysaccharide
2. Fewer steps and Scalable
3. Economic
4. Non-hazardous

DETAILED DESCRIPTION

The process of instant invention is related to a process for purification of antigenic polysaccharides.

The process of instant invention is quite robust which can be applied for purification of any polysaccharide, specifically antigenic polysaccharide.

The process of the instant invention affords polysaccharides of high quality.

The process of instant invention also affords the polysaccharides in high yields.

The process of the instant invention comprises following steps in any order:
a) treatment of the solution comprising polysaccharide with ammonium sulphate,
b) treatment of the solution comprising polysaccharide with nuclease,
c) isolation of the polysaccharide by adsorption chromatography.

More specifically, but not limited to, the process of the instant invention comprises following steps in any order:
a) precipitation of impurities using ammonium sulphate, followed by separation of supernatant
b) treatment of the solution comprising polysaccharide with nuclease, followed by separation of the polysaccharide containing phase
c) isolation of the polysaccharide by adsorption chromatography.

Specifically, in the process of instant invention the polysaccharide solution can be treated with ammonium sulphate to precipitate impurities. The mixture can be subjected to one or more unit operations to separate the precipitate. Centrifugation or filtration can be used to separate polysaccharide from other particulate or non-particulate matter based on the size of the polysaccharide and the other matter to be separated. The supernatant can be concentrated using ultrafiltration. The polysaccharide solution can be subjected to nuclease treatment. The mixture can be subjected to molecular weight or size based filtration, preferably ultrafiltration. The polysaccharide containing solution can be subjected to adsorption chromatography. The polysaccharide can be collected in the flow through. The solution containing pure polysaccharide can be subjected to concentration and sterilization.

Generally, the antigenic polysaccharides isolates are contaminated with proteins, nucleic acids, lipopolysaccharides and other impurities.

Polysaccharides devoid of these impurities are difficult to obtain. The instant invention provides a process to purify the polysaccharide with high yields and devoid of these and other impurities.

The polysaccharides of instant invention are the polysaccharides used as antigens in the vaccine preparation. More particularly, but not limited to, the polysaccharides are capsular polysaccharides used in the preparation of vaccines against Pneumococcal, Meningococcal or Hib infection.

The process of instant invention may employ concentration and dialysis/diafiltration step as and when required.

All steps of the process can be performed at room temperature. The process can also be performed at low temperature.

Specifically, crude polysaccharide serotypes can be concentrated using 100 KDa molecular weight cutoff ultrafiltration membrane. The concentrated crude can be diafiltered against 10 volumes of WFI. The polysaccharides can be treated with suitable concentration of ammonium sulphate to precipitate impurities without significant loss to the polysaccharide content. Specifically, the ammonium sulphate can be used in the range of 40-70% saturation. This step also removed color of the solution. The polysaccharides can be subjected to nuclease treatment at suitable temperature and duration. Specifically, the serotypes can be treated with nuclease at 25-37° C., for 4-12 hrs. The polysaccharides can be subjected to hydroxyl apatite chromatography and subsequently washed with 2-10 volumes of buffer containing sodium phosphate, wherein the pure polysaccharides can be afforded in the flow through and wash. The polysaccharide solution can then be subjected to concentration using suitable, preferably 100 KDa molecular weight cutoff membrane. The concentrated solution can be diafiltered against water for injection and subsequently lyophilized.

The process can be modified to change the sequence of the steps carried out to afford pure antigenic polysaccharide.

It is considered obvious to alter, modify or optimize the process of instant invention to obtain the polysaccharide with higher purity or yields. Repeating any or all steps in any order would certainly provide higher purity polysaccharide.

The purified polysaccharides comply with the WHO specifications for pure polysaccharides.

The following Examples further illustrate the essential features of the present invention. However, it will be apparent to those skilled in the art that the specific chemicals, apparatus, instruments, conditions and methods used in the Examples do not limit the scope of the present invention.

EXAMPLES

Example 1

S. Pneumoniae Capsular Polysaccharide Serotype 7F

Clarified broth 5L from the fermenter cultures of S. pneumoniae serotype 1 was concentrated to 500 ml and diafiltered using a 100 kDa MWCO membrane. Diafiltration was accomplished using 25 mM sodium phosphate buffer at neutral pH. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 66%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step recovery was about 77%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The polysaccharide solution was then concentrated using a 100 kDa MWCO membrane and then diafiltered with Water for Injection (WFI). The process step recovery was about 84%.

The diafiltered polysaccharide solution was filtered through a 0.22μ membrane filter into polypropylene bottles. The purified polysaccharide was stored frozen at −20±5° C. The overall process recovery was about 43%.

The protein content was 0.82%.
The nucleic acid content was 0.66%.
The endotoxin content was 7 IU/mg of polysaccharide.

Example 2

S. Pneumoniae Capsular Polysaccharide Serotype 18C

Clarified broth 5 L from the fermenter cultures of S. pneumoniae serotype 1 was concentrated to 500 ml and diafiltered using a 100 kDa MWCO membrane. Diafiltration was accomplished using 25 mM sodium phosphate buffer at neutral pH. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 74%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step recovery was about 66%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 75%.

The polysaccharide solution was then concentrated using a 100 kDa MWCO membrane and then diafiltered with Water for Injection (WFI).

The diafiltered polysaccharide solution was filtered through a 0.22μ membrane filter into polypropylene bottles. The purified polysaccharide was stored frozen at −20±5° C. The overall process recovery was 37%.

The protein content was not detectable.
The nucleic acid content was 0.57%.
The endotoxin content was 8 IU/mg of polysaccharide.

Example 3 i S. Pneumoniae Capsular Polysaccharide Serotype 9N

Clarified broth 5 L from the fermenter cultures of S. pneumoniae serotype 1 was concentrated to 500 ml and diafiltered using a 100 kDa MWCO membrane. Diafiltration was accomplished using 25 mM sodium phosphate buffer at neutral pH. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 79%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step recovery was about 81%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 69%.

The polysaccharide solution was then concentrated using a 100 kDa MWCO membrane and then diafiltered with Water for Injection (WFI).

The diafiltered polysaccharide solution was filtered through a 0.22µ membrane filter into polypropylene bottles. The purified polysaccharide was stored frozen at −20±5° C. The overall process recovery was about 44%.

The protein content was 0.50%,

The nucleic acid content was 0.71%.

The endotoxin content was 6 IU/mg of polysaccharide.

Example 4

S. Pneumoniae Capsular Polysaccharide Serotype 33F

Clarified broth 5L from the fermenter cultures of S. pneumoniae serotype 1 was concentrated to 500 ml and diafiltered using a 100 kDa MWCO membrane. Diafiltration was accomplished using 25 mM sodium phosphate buffer at neutral pH. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 53%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step ) recovery was about 82%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 94%.

The polysaccharide solution was then concentrated using a 100 kDa MWCO membrane and then diafiltered with Water for Injection (WFI).

The diafiltered polysaccharide solution was filtered through a 0.22µ membrane filter into polypropylene bottles. The purified polysaccharide was stored frozen at −20±5° C. The overall process recovery was about 41%.

The protein content was 0.94%.

The nucleic acid content was 0.97%.

The endotoxin content was 9 IU/mg of polysaccharide.

Example 5

S. Pneumoniae Capsular Polysaccharide Serotype 5

Clarified broth 5L from the fermenter cultures of S. pneumoniae serotype 1 was concentrated to 500 ml and diafiltered using a 100 kDa MWCO membrane. Diafiltration was accomplished using 25 mM sodium phosphate buffer at neutral pH. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 56%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step recovery was about 80%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 95%.

The polysaccharide solution was then concentrated using a 100 kDa MWCO membrane and then diafiltered with Water for Injection (WFI).

The diafiltered polysaccharide solution was filtered through a 0.22µ membrane filter into polypropylene bottles. The purified polysaccharide was stored frozen at −20±5° C. The overall process recovery was about 43%.

The protein content was not detectable.

The nucleic acid content was 0.18%.

The endotoxin content was 4 IU/mg of polysaccharide.

Example 6

S. Pneumoniae Capsular Polysaccharide Serotype 1

Clarified broth 5 L from the fermenter cultures of S. pneumoniae serotype 1 was concentrated to 500 ml and diafiltered using a 100 kDa MWCO membrane. Diafiltration was accomplished using 25 mM sodium phosphate buffer at neutral pH. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 65%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step recovery was about 92%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 70%.

The polysaccharide solution was then concentrated using a 100 kDa MWCO membrane and then diafiltered with Water for Injection (WFI).

The diafiltered polysaccharide solution was filtered through a 0.22μ membrane filter into polypropylene bottles. The purified polysaccharide was stored frozen at −20±5° C. The overall process recovery was 42%.

The protein content was not detectable.
The nucleic acid content was 0.9%.
The endotoxin content was 8 IU/mg of polysaccharide.

Example 7

*N. Meningitis* Capsular Polysaccharide Serotype A

Clarified broth 5 L from the fermenter cultures of *N. meningitidis* serotype A was concentrated to 500 ml and diafiltered using a 100 kDa MWCO membrane. Diafiltration was accomplished using WFI. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 300 kDa MWCO membrane. The process step recovery was about 52%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 300 kDa MWCO membrane. The process step recovery was about 81%, The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 95%.

The polysaccharide solution was then concentrated using a 100 kDa MWCO membrane and then diafiltered with Water for Injection (WFI).

The diafiltered polysaccharide solution was filtered through a 0.22μ membrane filter into polypropylene bottles. The purified polysaccharide was stored frozen at −20±5° C. The overall process recovery was 40%.

The protein content was not detectable.
The nucleic acid content was 0.9%.
The endotoxin content was 7 IU/mg of polysaccharide.

Example 8

*H. influenzae* Capsular Polysaccharide Serotype b

Clarified broth 5 L from the fermenter cultures of *H. influenzae* serotype b was concentrated to 500 ml and diafiltered using a 100 kDa MWCO membrane. Diafiltration was accomplished using WFI. Ammonium sulphate was added to the concentrate to 50% saturation and incubated at 2-8° C. for 12 hrs. The mixture was subjected to centrifugation. The pellet (precipitate) was discarded. The solution (500 ml) containing polysaccharide was concentrated and diafiltered (20×) against 20 mM Tris HCl, 2 mM MgCl2 pH 8.0±0.2, using 100 kDa MWCO membrane. The process step recovery was about 74%.

Endonuclease was added to the polysaccharide solution to achieve a final concentration of 8 U/ml of solution. The enzyme treatment was carried out at 37° C., for 12 hrs. The mixture was then subjected to concentration and diafiltration (20×) against 20 mM sodium phosphate pH 7.2±0.2, using 100 kDa MWCO membrane. The process step recovery was about 95%.

The hydroxyl apatite column (300 ml) was equilibrated with 20 mM sodium phosphate buffer, pH 7.2±0. The polysaccharide solution (500 ml) was then loaded onto the column and the column was washed with the buffer. Under these conditions, the polysaccharide was recovered in the flow-through and equilibration wash from the column. The process step recovery was about 72%.

The polysaccharide solution was then concentrated using a 100 kDa MWCO membrane and then diafiltered with Water for Injection (WFI).

The diafiltered polysaccharide solution was filtered through a 0.22μ membrane filter into polypropylene bottles. The purified polysaccharide was stored frozen at −20±5° C. The overall process recovery was about 51%.

The protein content was 0.9%.
The nucleic acid content was 0.5%.
The endotoxin content was 9 IU/mg of polysaccharide.

REFERENCES

1. Whitney C G, Farley M M, Hadler J, et al. Decline in invasive pneumococcal disease after the introduction of polysaccharide conjugate vaccine. New Engl J Med 2003, 348 (18); 1737-46.
2. Black S, Shinefield H, Hansen J et al. postlicensure evaluation of the effectiveness of seven valent pneumococcal conjugate vaccine. Pediatr Infect Dis J 2001; 20; 1105-7.
3. Institute Merieux (1980) Brevet Beige (Patent No.) 80 26320.
4. Yavordios D. and Cousin, M (1983) European Patent 0071515 A1
5. Applied and environmental microbiology, February 2001, p. 969-971, Vol. 67, No. 2, Production of capsular polysaccharide of *Streptococcus pneumoniae* Type 14 and it's purification by Affinity chromatography
6. Tanizaki, M. M., Garcia, L. R, Ramos, J. B., Leite, L. C. C., H., Furuta, J. A., Cabrera-Crespo, J. and raw, I, (1996) J. Microbiol. Methods 27, 19-23.
7. Ayme, G., Donikian, R., Mynard, M. C. and Lagrandeur, G (1973) in Table ronde sur "immunoprophylaxie de la meningite cerebro-spinale (triav, R, ed) pp. 4, fondation Merieux, Lyon.
8. Viviane Maimoni M. et. al., Purification of capsular polysaccharide from *Streptococcus pneumoniae* serotype 23 F by a procedure suitable for scale up, Biotechgnol. Appl. Biochem. (2003) 37, 283-287.
9. Suarez, N, Fraguas, L F., Teixeira, E., Massaoldi, H., Batista-Viera, F and Ferreira, F. (2001) Appl. Environ. Microbiol. 67, 969-971.
10. Hausdorff; William P.; et al. (Wyeth) Multivalent pneumococcal polysaccharide-protein conjugate composition (2006), US patent application No. 20060228380.
11. Arnold; Frank Josef (Newfoundland, Pa.), Soika; Michael (Spring Valley, N.Y.), (1998), Alcohol-free pneumococcal polysaccharide purification process, U.S. Pat. No. 5,714,354

12. Kniskern; Peter J. (Lansdale, Pa.), Miller; William J. (North Wales, Pa.), Hagopian; Arpi (Lansdale, Pa.), Ip; Charlotte C. (Blue Bell, Pa.), Hennessey, Jr.; John P. (Dublin, Pa.), Kubek; Dennis J. (Salem, W. Va.), Burke; Pamela D. (Lansdale, Pa.), (1998) Process for making capsular polysaccharides from Streptococcus pneumoniae, U.S. Pat. No. 5,847,112.

We claim:

1. A detergent and organic solvent free process for preparing a purified antigenic polysaccharide which comprises:
   a) Concentrating the polysaccharide solution by ultrafiltration using a 100 KDa molecular weight cutoff membrane to remove low molecular weight contaminants to form a solution of concentrated polysaccharide;
   b) Precipitating the concentrated polysaccharide solution with ammonium sulphate to form a partially purified polysaccharide solution;
   c) Ultrafiltration and diafiltration with a buffer to remove soluble contaminants and ammonium sulphate;
   d) Collecting the resulting polysaccharide solution;
   e) Addition of benzonase to remove nucleic acids;
   f) Ultrafiltration and diafiltration with sodium phosphate buffer to remove nuclease and nucleic acids;
   g) Subjecting the polysaccharide solution from step (f) to hydroxyl apatite chromatography;
   h) Collecting the eluate from step (g) for further concentration, ultrafiltration and diafiltration against WFI; and
   i) Subjecting the eluate to 0.22 micron filtration.

2. The process according to claim 1, wherein step (b) utilizes a concentration of about 50% ammonium sulphate.

3. The process according to claim 1, wherein step (c) utilizes a buffer selected from a group consisting of phosphate, citrate, Tris and HEPES.

4. The process according to claim 3, wherein the concentration of Tris buffer in step (c) is 20 mM, and a concentration of $MgCl_2$ is 2 mM.

5. The process according to claim 1, wherein the final concentration of benzonase is 8 U/ml of polysaccharide solution.

6. The process according to claim 1, wherein the yield of the polysaccharide is in the range of 30-60%.

7. The process according to claim 1, wherein the purity of the polysaccharide is at least 98% relative to the total weight of polysaccharide, protein and nucleic acid in the composition.

8. The process according to claim 1, wherein the antigenic polysaccharide obtained contains endotoxin less than 10 IU/mg of polysaccharide 9. The process according to claim 1, wherein step (g) comprises:
   (a) diafiltration of the polysaccharide solution with 20 mM phosphate buffer pH 7.2;
   (b) equilibration of the hydroxyl apatite column with 20 mM phosphate buffer pH 7.2;
   (c) applying the polysaccharide solution from step (b) on a hydroxyl apatite column; and
   (d) washing the column with 4 to 8 column volumes of buffer.

10. The process according to claim 1, wherein the polysaccharide eluate is concentrated and diafiltered on 300 kDa ultrafiltration membrane.

11. The process according to claim 1, wherein the polysaccharide is from a bacteria selected from the group consisting of *Streptococcus pneumoniae, Haemophilus influenzae, Neisseria meningitides* .

12. A detergent and organic solvent free process for comprises:prepatin a purified antigenic polysaccharide from *Streptococcus pneumoniae* which
   a) Concentrating the polysaccharide solution by ultrafiltration using a 100 KDa molecular weight cutoff membrane to remove low molecular weight contaminants to form a solution of concentrated polysaccharide;
   b) Precipitating the concentrated polysaccharide solution with ammonium sulphate to form a partially purified polysaccharide solution;
   c) Ultrafiltration and diafiltration with a buffer to remove soluble contaminants and ammonium sulphate;
   d) Collecting the resulting polysaccharide solution;
   e) Addition of nucleases to remove nucleic acids;
   f) Ultrafiltration and diafiltration with sodium phosphate buffer to remove nuclease and nucleic acids;
   g) Subjecting the polysaccharide solution from step (f) to hydroxyl apatite chromatography;
   h) Collecting the eluate from step (g) for further concentration, ultrafiltration and diafiltration against WFI; and
   i) Subjecting the eluate to 0.22 micron filtration,
   wherein the polysaccharide is derived from any of the subtypes of *Streptococcus pneumoniae* selected from 1, 2, 3, 4, 5, 6B, 7F, 8, 9N, 9V, 10A, 11A, 12F, 14, 15B, 17F, 18C, 19F, 19A, 20, 22F, 23F, and 33F.

13. A detergent and organic solvent free process for preparing a purified antigenic polysaccharide from *Neisseria meningitides* which comprises:
   a) Concentrating the polysaccharide solution by ultrafiltration using a 100 KDa molecular weight cutoff membrane to remove low molecular weight contaminants to form a solution of concentrated polysaccharide;
   b) Precipitating the concentrated polysaccharide solution with ammonium sulphate to form a partially purified polysaccharide solution;
   c) Ultrafiltration and diafiltration with a buffer to remove soluble contaminants and ammonium sulphate;
   d) Collecting the resulting polysaccharide solution;
   e) Addition of nucleases to remove nucleic acids;
   f) Ultrafiltration and diafiltration with sodium phosphate buffer to remove nuclease and nucleic acids;
   g) Subjecting the polysaccharide solution from step (f) to hydroxyl apatite chromatography;
   h) Collecting the eluate from step (g) for further concentration, ultrafiltration and diafiltration against WFI; and
   i) Subjecting the eluate to 0.22 micron filtration,
   wherein the polysaccharide is derived from any of the subtypes of *Neisseria meningitides* selected from a group consisting of A, C, Y and W-135.

14. The process according to claim 1, wherein the polysaccharide is further derivatized or sized before or while using as a vaccine component.

15. The process according to claim 1, wherein the polysaccharide is used in a monovalent, divalent or multivalent vaccine and is free, conjugated or complexed.

16. The process according to claim 12 wherein said nucleases comprise benzonase.

17. The process according to claim 13 wherein said nucleases comprise benzonase.

18. A detergent and organic solvent free process for preparing a purified antigenic polysaccharide from *Haemophilus influenzae* which comprises:
   a) Concentrating the polysaccharide solution by ultrafiltration using a 100 KDa molecular weight cutoff membrane to remove low molecular weight contaminants to form a solution of concentrated polysaccharide;

b) Precipitating the concentrated polysaccharide solution with ammonium sulphate to form a partially purified polysaccharide solution;

c) Ultrafiltration and diafiltration with a buffer to remove soluble contaminants and ammonium sulphate;

d) Collecting the resulting polysaccharide solution;

e) Addition of nucleases to remove nucleic acids;

f) Ultrafiltration and diafiltration with sodium phosphate buffer to remove nuclease and nucleic acids;

g) Subjecting the polysaccharide solution from step (f) to hydroxyl apatite chromatography;

h) Collecting the eluate from step (g) for further concentration, ultrafiltration and diafiltration against WFI; and i) Subjecting the eluate to 0.22 micron filtration, wherein the polysaccharide is derived from *Haemophilus influenzae* subtype b.

19. The process according to claim 18 wherein said nucleases comprise benzonase.

* * * * *